United States Patent [19]
Szabo

[11] Patent Number: 5,913,846
[45] Date of Patent: Jun. 22, 1999

[54] SHIELDED NEEDLE ASSEMBLY

[75] Inventor: Sandor Szabo, Elmwood Park, N.J.

[73] Assignee: Becton, Dickinson and Company, Franklin Lakes, N.J.

[ * ] Notice: This patent is subject to a terminal disclaimer.

[21] Appl. No.: 08/662,387

[22] Filed: Jun. 13, 1996

[51] Int. Cl.⁶ .................................................. A61M 5/00
[52] U.S. Cl. ........................ 604/263; 604/192; 604/198; 128/919
[58] Field of Search ................................... 604/181, 187, 604/263, 192, 198, 110; 128/919

[56] References Cited

U.S. PATENT DOCUMENTS

| | | |
|---|---|---|
| 4,982,842 | 1/1991 | Hollister. |
| 5,116,325 | 5/1992 | Paterson ................................. 604/192 |
| 5,152,751 | 10/1992 | Kozlowski .............................. 604/192 |
| 5,207,653 | 5/1993 | Janjua et al. ............................ 604/192 |
| 5,445,619 | 8/1995 | Burns ...................................... 128/919 |
| 5,462,534 | 10/1995 | Debreczeni ............................. 604/192 |
| 5,584,816 | 12/1996 | Gyure et al. ............................ 604/192 |
| 5,599,313 | 2/1997 | Gyure et al. ............................ 604/192 |
| 5,599,318 | 2/1997 | Sweeney et al. ....................... 604/263 |
| 5,603,699 | 2/1997 | Shine ...................................... 604/263 |
| 5,632,732 | 5/1997 | Szabo et al. ............................ 604/187 |
| 5,662,617 | 9/1997 | Odell et al. ............................. 604/192 |
| 5,702,369 | 12/1997 | Mercereau .............................. 604/192 |

*Primary Examiner*—Ronald Stright
*Attorney, Agent, or Firm*—Arthur D. Dawson

[57] ABSTRACT

A shielded needle assembly including an elongate needle with a proximal end, a distal end and a passageway therethrough. The assembly has a needle hub with a proximal end, a distal end and an outside surface. The proximal end of the needle is fitted and held in an axial opening through the needle hub at the distal end of the needle hub, with the distal end of the needle projecting distally axially. The proximal end of the needle hub is configured for releasable mounting the needle hub on a fluid handling device. The assembly of the invention has a shield with an open proximal end, a distal end, a sidewall having an elongate opening extending from the proximal end to the open end. The shield is operative between an open position, where the needle is exposed for use by passage through the elongate opening, a closed position, where the shield substantially obstructs access to the needle, and a latched position, where the shield is substantially prevented from inadvertent movement to the open position. The shield is attached to the needle hub by a mount with a hinge. The shield is movable between the open position and the closed position by an off axis pivotal movement about the hinge, and between the closed position and the latched position by an axial movement of the shield with respect to the mount.

4 Claims, 15 Drawing Sheets

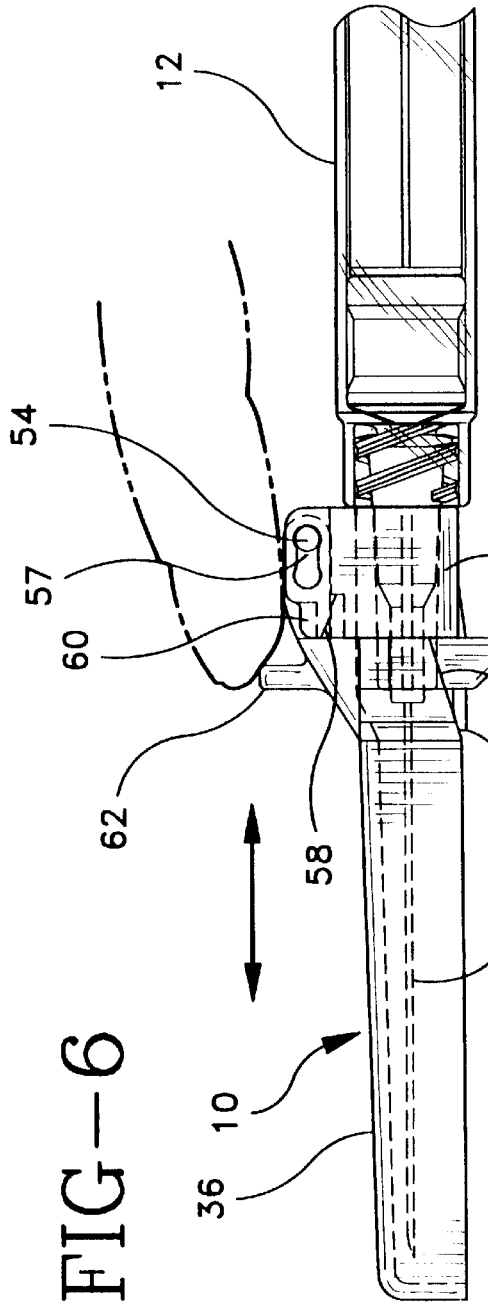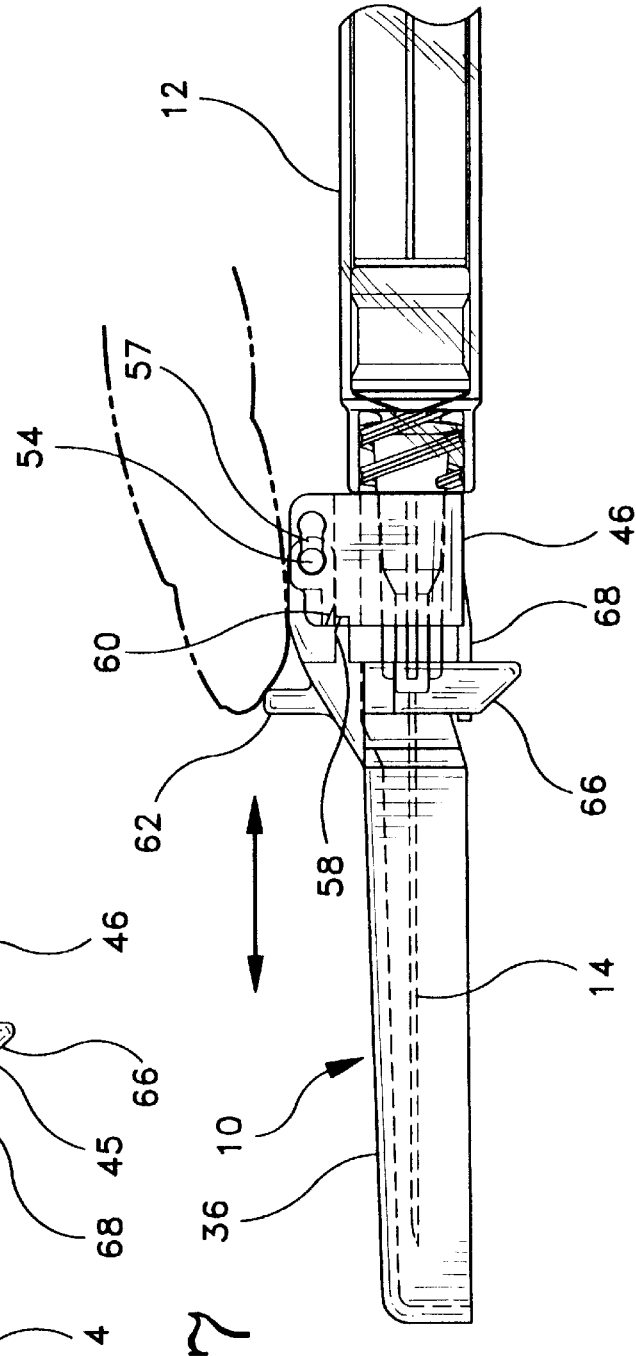
FIG-6
FIG-7

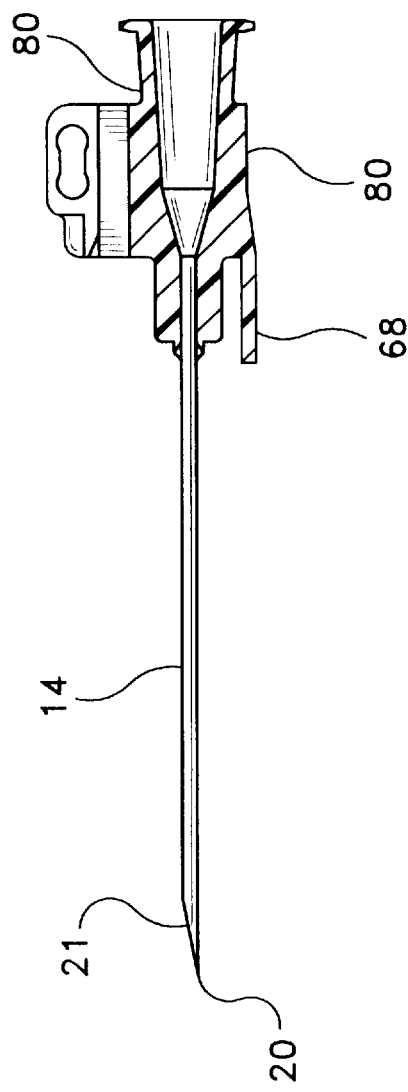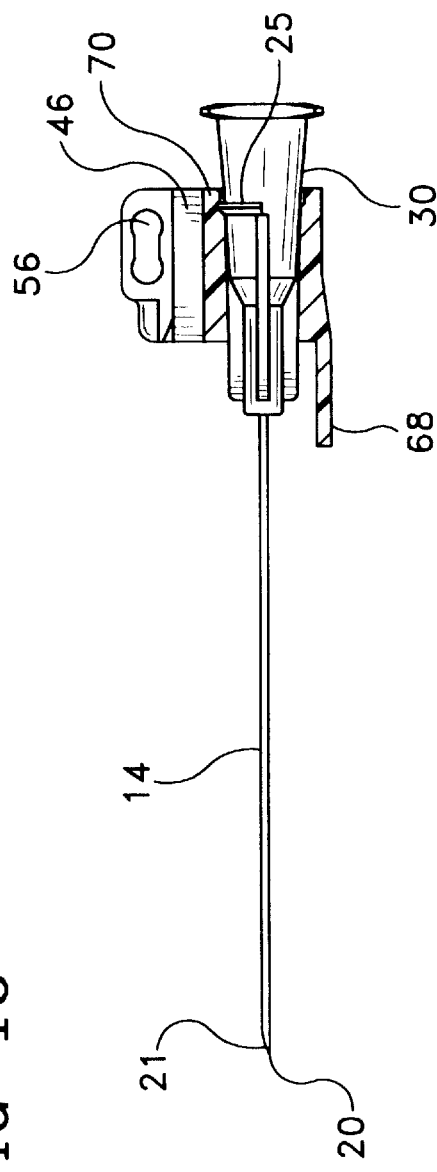

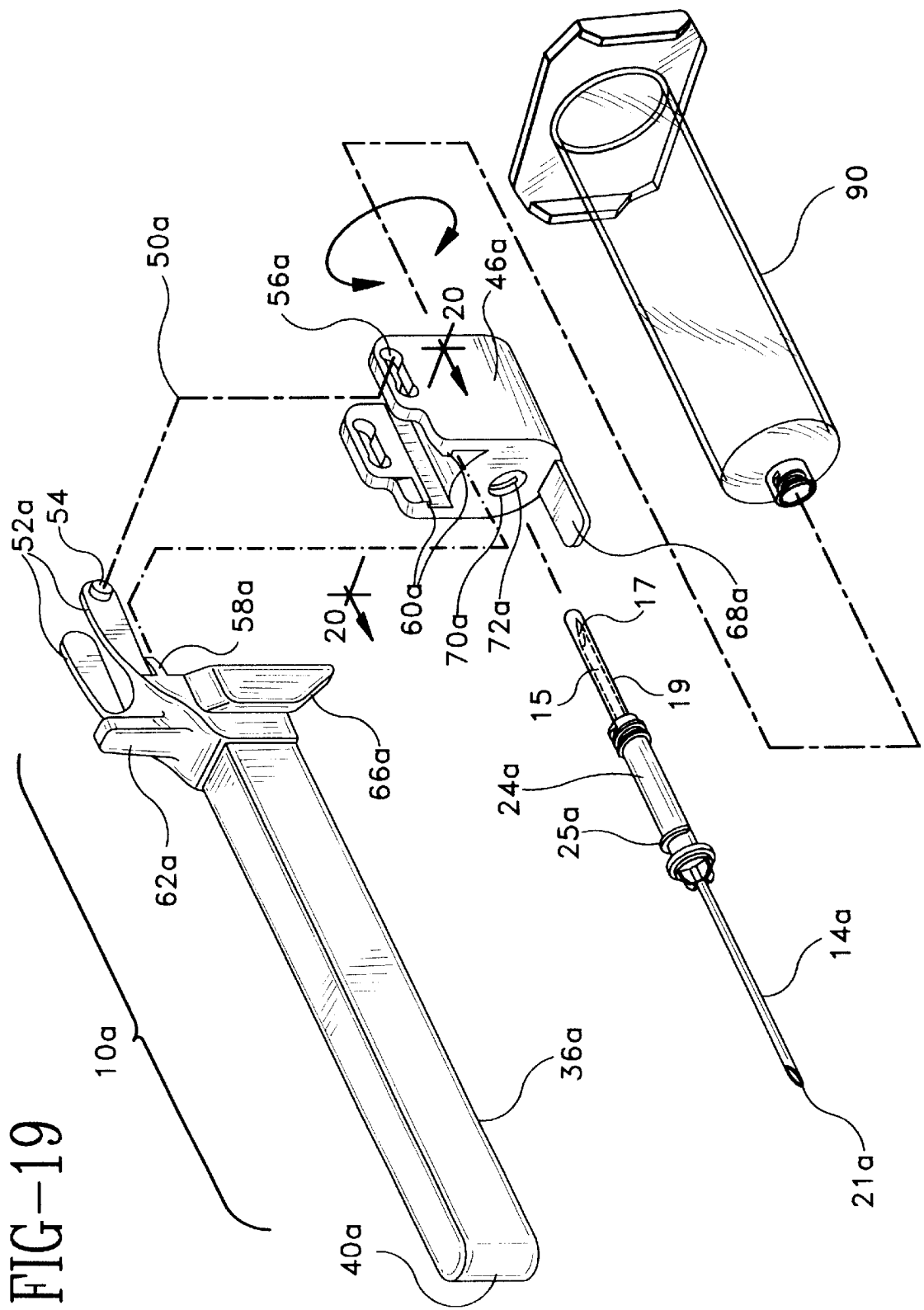

SHIELDED NEEDLE ASSEMBLY

FIELD OF INVENTION

The present invention relates to a protective shield for a needle and more particularly to a shield assembly that includes the hub of the needle, and allows use of the needle on a syringe, needle holder or other fluid handling device.

DESCRIPTION OF RELATED INFORMATION

In the medical arts, sharp pointed needles are used for a variety of procedures. Devices having sharp pointed needles are used for administering fluids to patients either directly or into intravenous apparatus, and in various blood drawing applications either with syringes or with specialized holders for filling evacuated tubes.

Exposure to blood borne pathogens should be a recognized hazard by anyone associated with the medical arts. As a result of this recognition, numerous protocols for use of needles have been developed and are widely practiced. The problem of transmission of blood borne pathogens not only exists for the physician, nurse or phlebotomist using the needles, but also for support workers all through the hospital. Since most needles in use today are single-use and disposable, hospital service personnel, e.g., laundry, housekeeping, etc., are at risk from needles that are not properly handled by the users.

The use protocols generally dictate in detail when and how a needle is used and how it should be disposed of The problem with many protocols for handling needles is that the protocols often require users to perform additional steps in a procedure. With the press of time and simple carelessness, certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing other workers to used needles. A representative listing of many of these devices is found in U.S. Pat. No. 4,982,842 to Hollister et al. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead-space" volume of the device on which the adapter is mounted, requires an additional part which increases the projection of the needle hub. Also, if bevel position is important to the intended use of the needle, the Hollister et al. invention must be carefully aligned with the needle point when the needle hub is mounted onto the Hollister et al. device.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely with the hub oriented during assembly, the shield may interfere in some applications.

The Hollister et al. patent and the Janjua et al. patent attempt to address the recognized need to protect medical and service personnel from needle sticks. There are several recurrent problems in varying degrees with these devices. Many of these previous devices are somewhat complex, hence are significantly more costly than an unprotected device. Many of these previous devices also increase the complexity or increase the difficulty of performing a procedure. Some others of the previous devices are so procedure specific that they preclude use of the device in certain other procedures. For these and similar reasons most of the devices disclosed in the Hollister et al. background of about ninety patents have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in Janjua et al., while there is a recognition of the need to secure the cap in the closed position over the needle, all of the solutions proposed require additional steps such as securing the cap with an adhesive or twisting the cap.

Although there already are many shielded needle devices, there is still a need for a shielded needle device that is easily manufactured, applicable to many fluid handling devices, as well as simple and intuitive to use. Additionally, the needle device should not interfere with normal practices of use. Such a device is described below.

SUMMARY

A shielded needle assembly of the present invention includes an elongate needle with a proximal end, a distal end and a passageway therethrough. The assembly of the invention has a needle hub with a proximal end, a distal end and an outside surface. The proximal end of the needle is fitted and held in an axial opening through the needle hub, with the distal end of the needle projecting distally axially from the needle hub. The proximal end of the needle hub is configured for releasably mounting the needle hub on a fluid handling device. The assembly of the invention has an elongate shield with an open proximal end, a distal end, a sidewall having an elongate opening extending from the distal end to the open proximal end. The shield is operative between an open position, where the needle is exposed for use by passage through the elongate opening; a closed position, where the shield substantially obstructs access to the needle; and a latched position, where the shield is substantially prevented from inadvertent movement to the open position. The shield is attached to the needle hub by a mount with a hinge. The shield is movable between the open position and the closed position by an off axis pivotal movement about the hinge, and between the closed position and the latched position by an axial movement of the shield with respect to the mount.

The shielded needle assembly of the invention has an ergonomic design that to allows an operator to intuitively operate the shield between the latched, closed and open positions while holding a fluid handling device in one hand as is customary for most applications. The latched position substantially prevents inadvertent exposure of the needle. When the shield is latched, it is easily and intuitively released by moving the shield distally with respect to the needle hub and mount. After being unlatched, the shield of the invention is then easily opened and closed by a pivotal movement to expose and cover the needle. When in the closed position, the shield is easily relatched by a simple proximal movement of the shield with respect to the mount. When open, the shield is pivotable, and, preferably has a mount that allows the shield to be rotatable about the hub to be substantially out of the way for particular procedures. Since the shielded needle assembly of the invention includes the needle hub, it imposes few constraints on the types of fluid handling devices or procedures for which it is may be used. Unlike the previous devices, the shielded assembly of the invention does not add to the dead-space volume of the fluid handling device. The shielded assembly of the invention is simple, having only two more parts than a standard unshielded needle assembly and it is easy to manufacture.

BRIEF DESCRIPTION OF THE DRAWINGS

FIG. 6 is a schematic side elevation of the shielded needle assembly of the present invention with the shield in the latched position;

FIG. 7 is a schematic side elevation of the shielded needle assembly of the present invention, analogous to the view of FIG. 6, with the in the closed position;

FIG. 16 is a partial cross-sectional view of an embodiment of the needle, hub and mount of the assembly of the invention;

FIG. 18 is a partial cross-sectional view of the needle, hub and mount of the needle assembly of the invention shown in FIG. 17;

FIG. 19 is a partially exploded perspective view of an embodiment of the needle, hub and mount of the invention for use on a needle holder;

DETAILED DESCRIPTION

Figure 1:
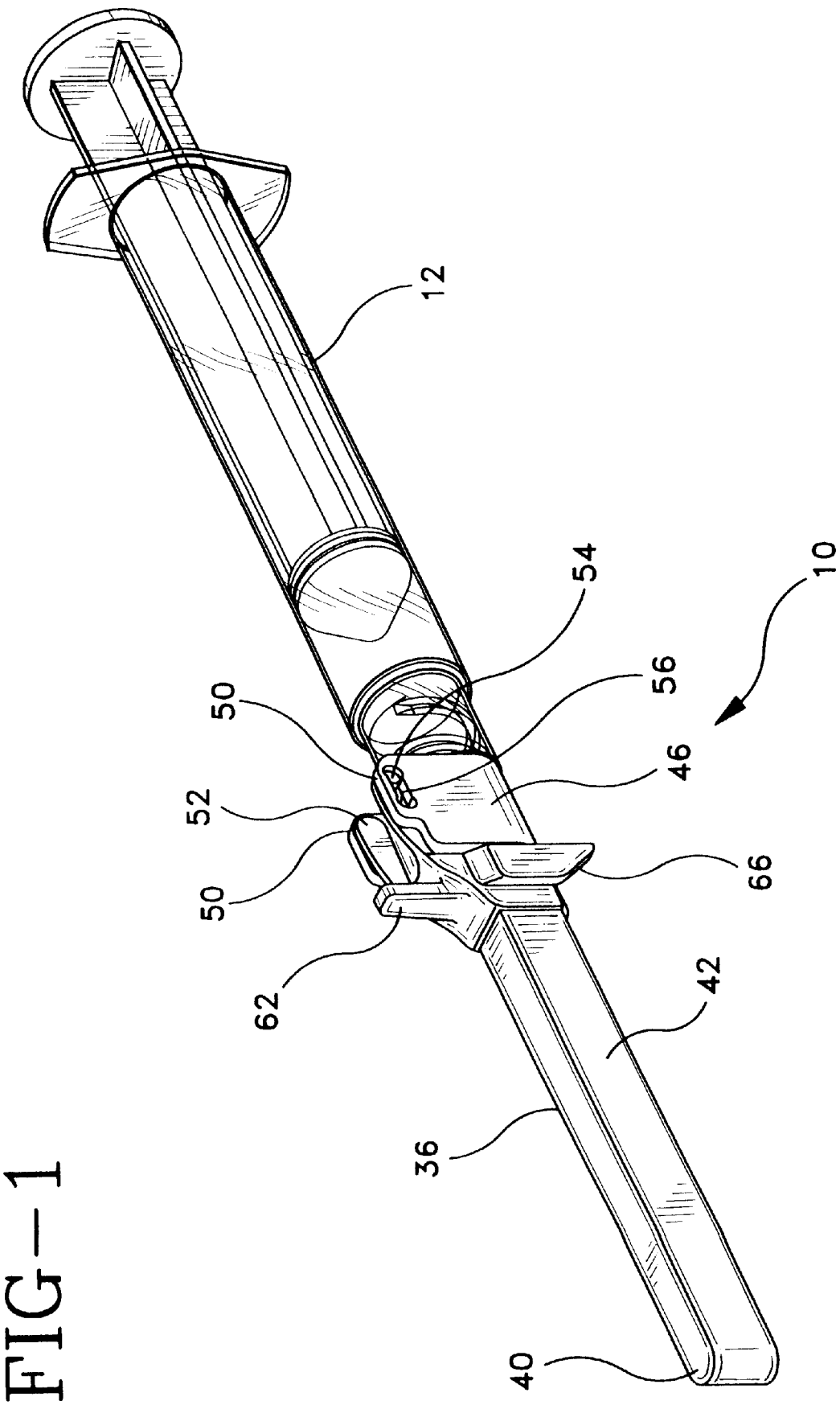
FIG. 1 is a perspective view of a shielded needle assembly of the present invention as mounted on a syringe and with the shield in the latched position.

While this invention is satisfied by embodiments in many different forms, there are shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

Referring to FIGS. 1–15, a preferred needle assembly 10 of the present invention, shown mounted on a syringe 12, includes an elongate needle 14 that has a proximal end 16, a distal end 18, preferably with a sharp point 20, a beveled surf and a passageway 22 therethrough. Assembly 10 has a needle hub 24 with a proximal end 26, a distal end 28, and an outside surface 30. Needle hub 24 has an axial opening 32 therethrough to receive and hold proximal end 16 of the needle with distal end 18 projecting axially outwardly. Preferably, needle hub proximal end 26 has a female luer fitting 34 to facilitate attaching the assembly to a fluid handling device such as a syringe. For other applications, proximal end 26 may include fittings such as external threads to facilitate attachment of the assembly to blood collection devices and the like.

Figure 2:
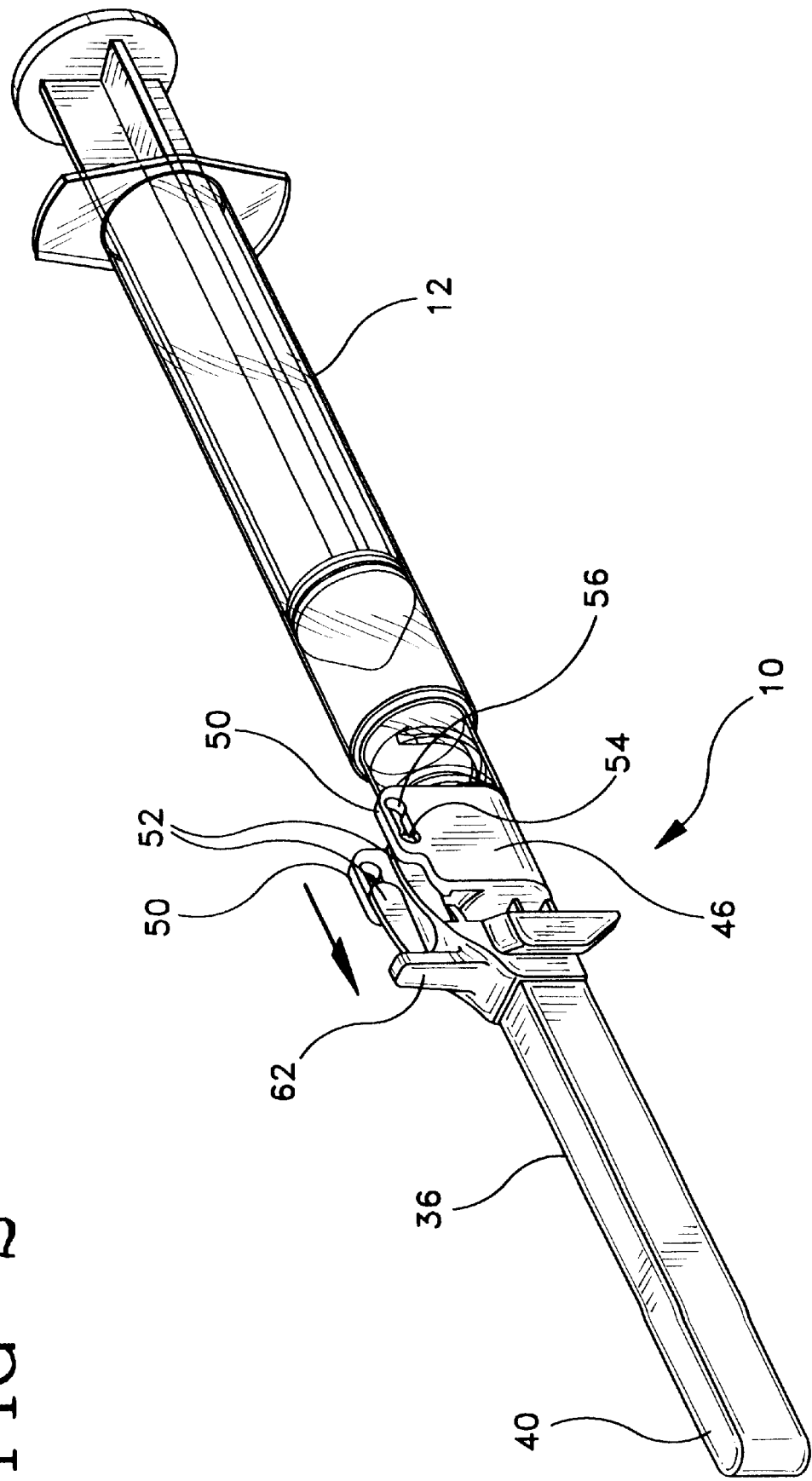
FIG. 2 is a perspective view of the of the assembly of FIG. 1 with the shield in the closed position.
Figure 3:
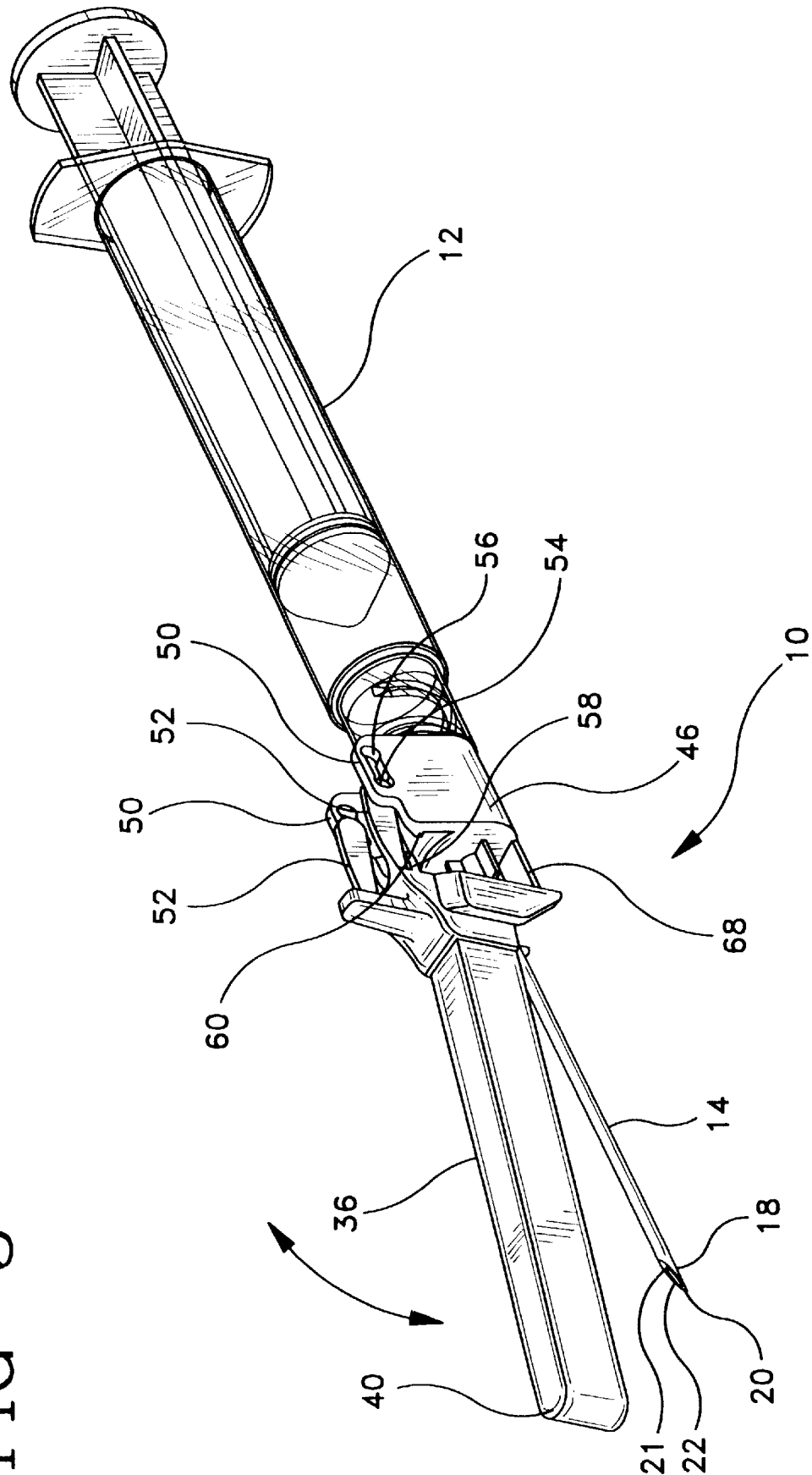
FIG. 3 is a perspective view of the assembly of FIG. 1 with the shield partially opened.
Figure 4:
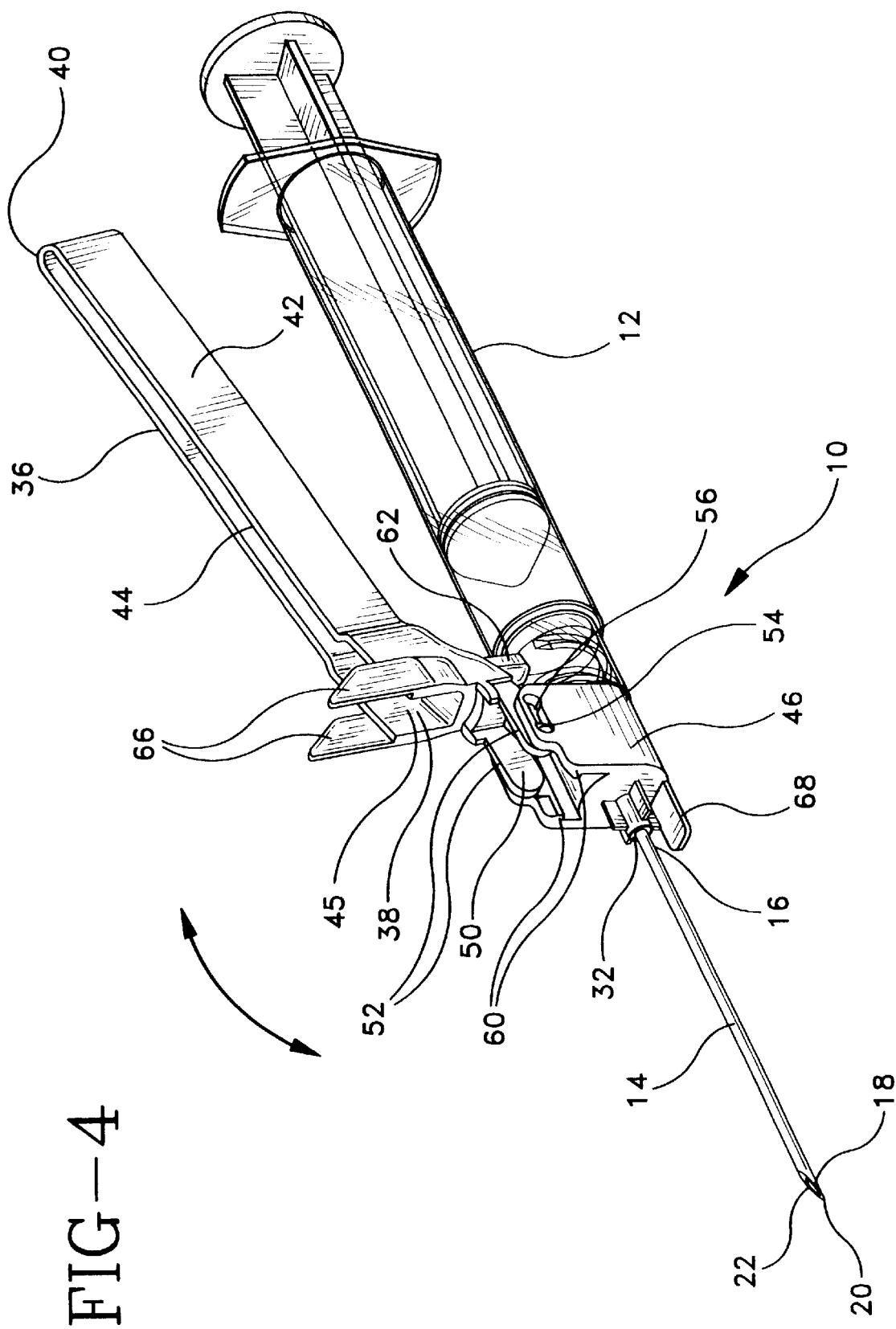
FIG. 4 is a perspective view of the assembly of FIG. 1 with the needle fully exposed.
Figure 5:
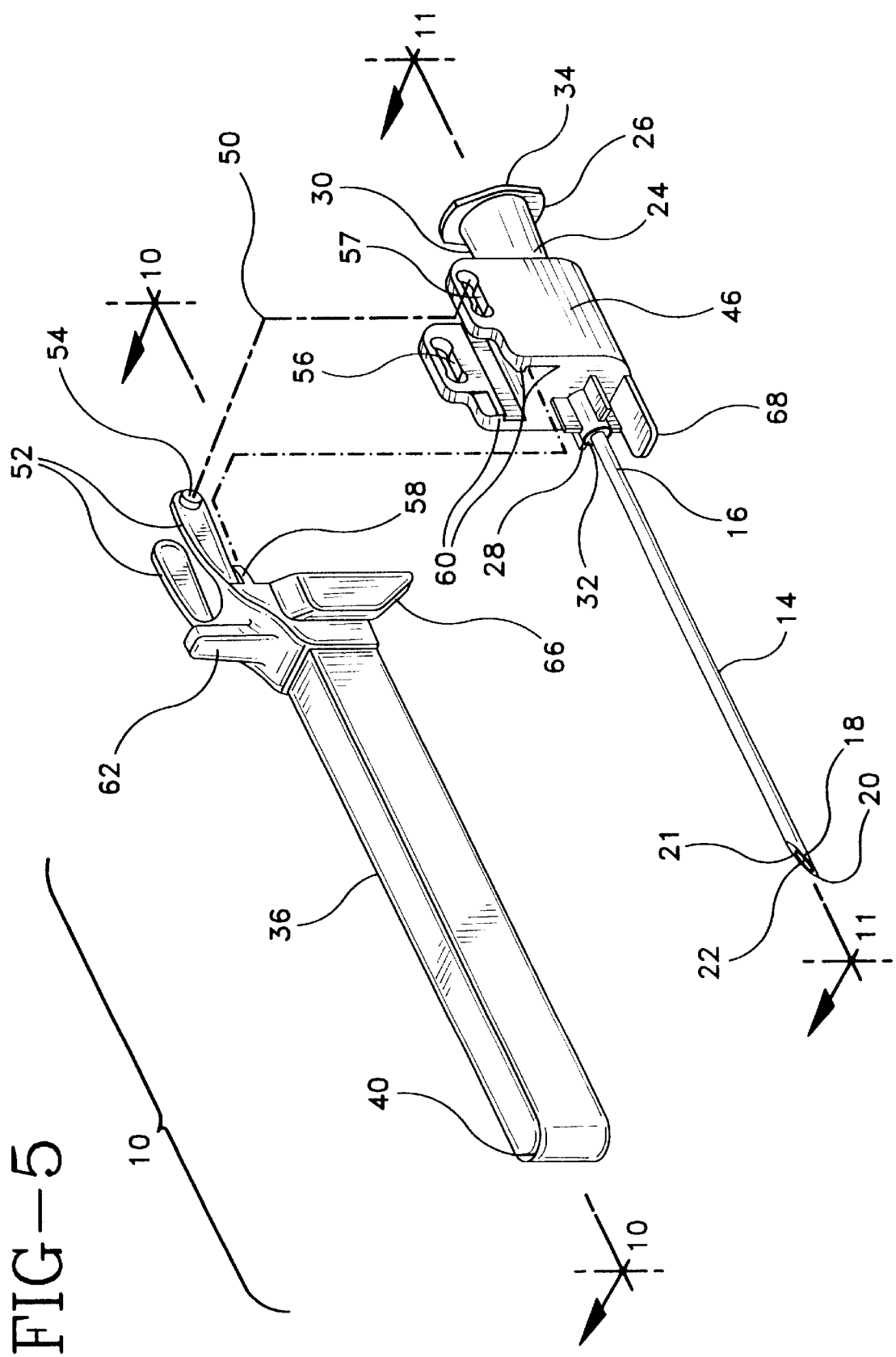
FIG. 5 is a partially exploded perspective view of the shielded needle assembly of the present invention.

Assembly 10 has an elongate shield 36 with a proximal open end 38, a distal, preferably closed, end 40, a sidewall 42 with an elongate opening 44 extending from distal end 40 to open end 38. Shield 36 is operative between a latched position, as shown in FIG. 1, a closed unlatched position, as shown in FIG. 2, and open positions, as shown in FIGS. 3 and 4. Shield 36 is attached to a mount 46 that serves to hold the shield onto the needle hub with a hinge 50 that allows off-axis pivotal movement of the shield between the closed position and the open position and between the latched position and the closed position by an axial movement of the shield with respect to the mount as shown in FIGS. 1 and 2. Mount 46 has a passage 48 to receive at least a portion of needle hub 26.

Preferably, hinge 50 includes two arms 52 projecting proximally axially from proximal open end 38 of the shield. Arms 52 each have outwardly extending, preferably perpendicular, pegs 54 and mount 46 has a pair of elongate slots 56 sized and disposed to receive pegs 54 forming hinge 50 and attaching shield 36 to mount 46. Axial movement of shield 36, with respect to mount 46, between the latched and unlatched closed positions, is substantially defined by the axial travel of pegs 54 in slots 56.

Assembly 10 is latched and unlatched, best seen in FIGS. 5–8, by operative engagement and disengagement of tabs 58 projecting outwardly on the shield proximal open end 38 with ledges 60 that project inwardly on mount 46. When shield 36 is proximal with respect to the mount, tabs 58 engage ledges 60, best seen in FIG. 6, substantially preventing pivotal movement of shield 35 about hinge 50 to the open position. Conversely, assembly 10 is unlatched, best seen in FIGS. 7 and 8, by distal movement of shield 36 with respect to mount 46. Preferably, elongate slots 56 each include a detent 57 formed by a narrowed area that provides a tactile indication of movement of pegs 54 between positions corresponding to the closed and latched positions of the shield. Detent 57 substantially prevents inadvertent movement of the shield between the closed (unlatched) position and the latched position.

Figure 8:
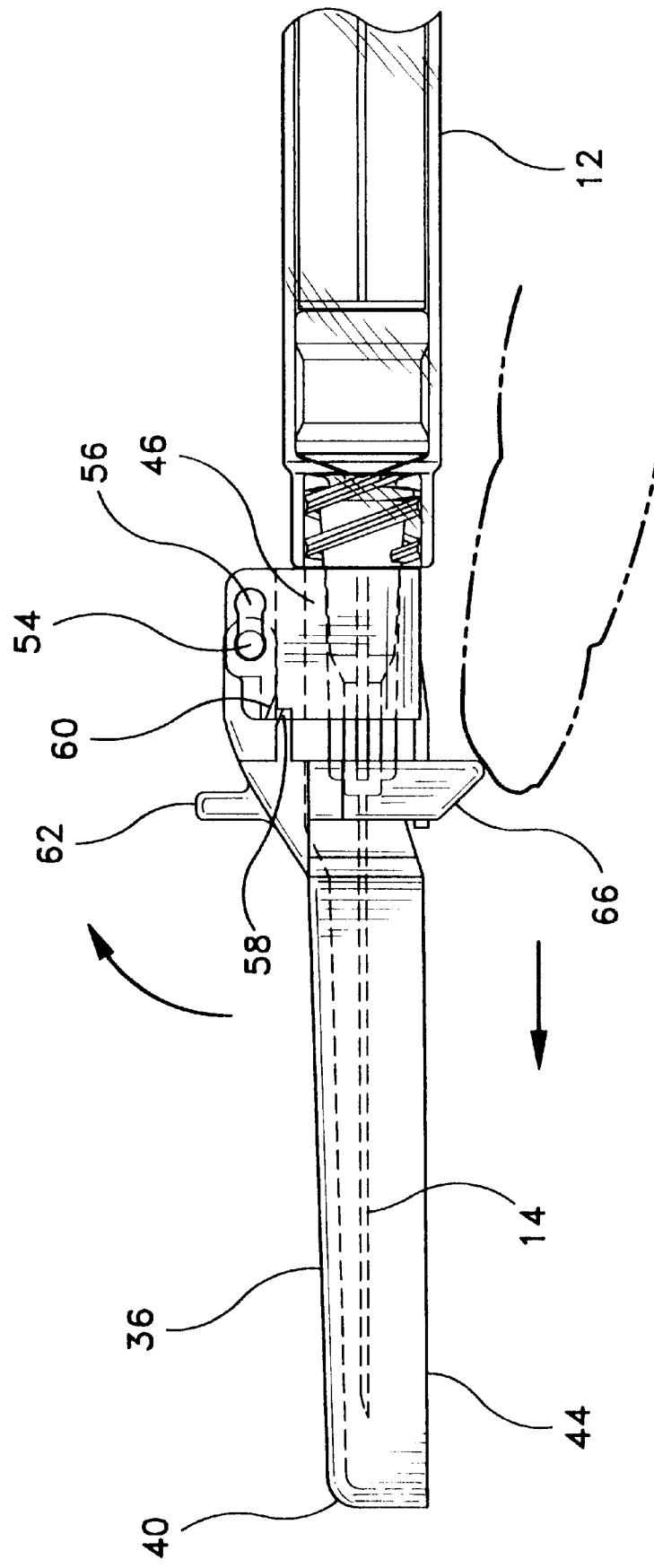
FIG. 8 is a schematic side elevation of the shielded needle assembly of the present invention, analogous to the view of FIG. 6, with the shield in the closed position, ready to be moved to the open position.

As is seen in FIG. 8, tabs 58 preferably disengage from ledges 60, but are not fully distal to the ledges. This preferred disposition of the tabs to the ledges in the unlatched position, results in tabs 58 marginally contacting and deflecting ("bumping past") the ledges when shield 36 pivots about hinge 50 between the closed (unlatched) position shown in FIG. 8 and the open (needle exposed) position shown in FIG. 9. The tabs bumping past the ledges during pivotal movement provides a slight restraint that tends to maintain the shield in the position it is placed by the practitioner.

Figure 9:
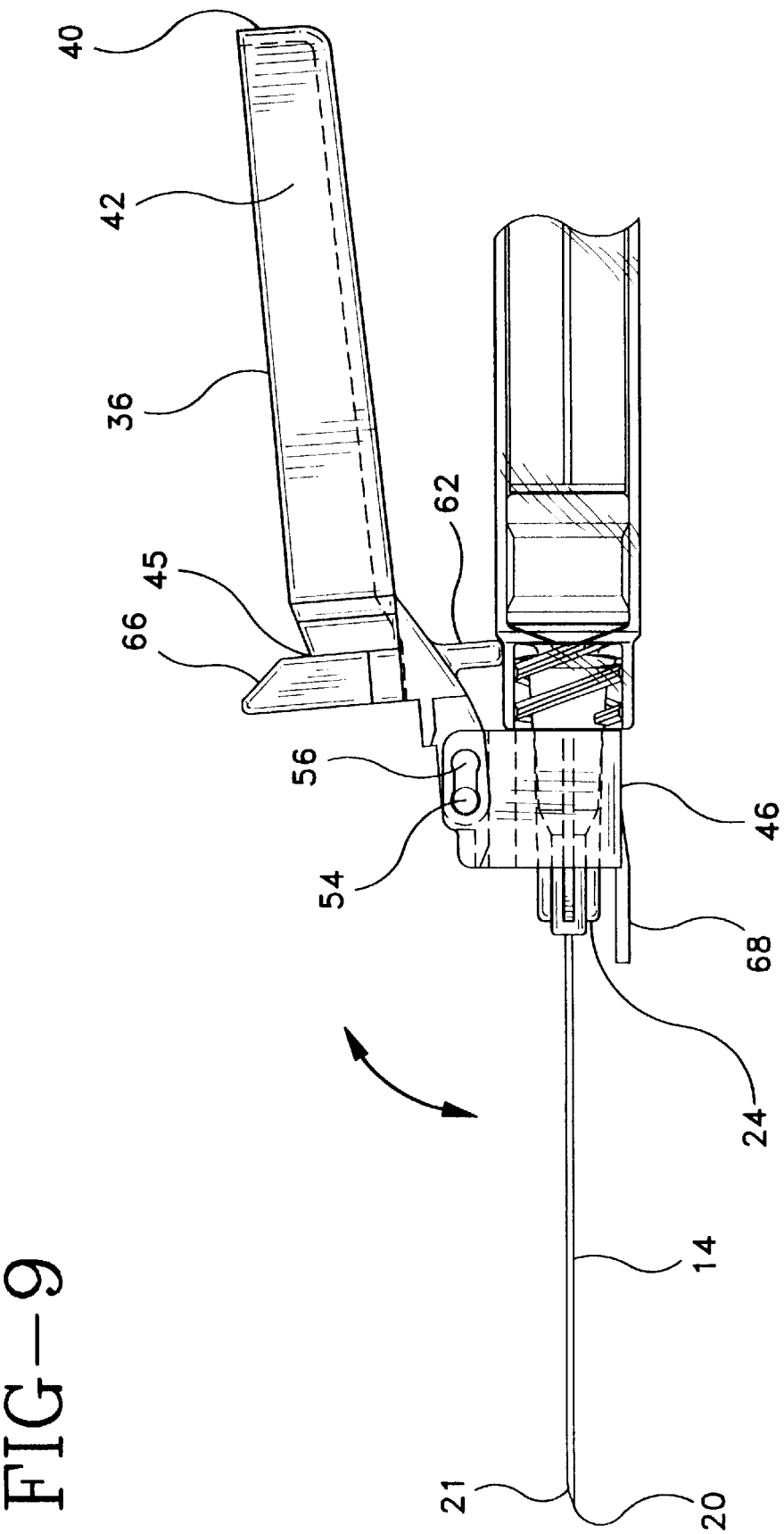
FIG. 9 is a schematic side elevation of the shielded needle assembly of the present invention, analogous to the view of FIG. 6, with the shield in the open position and the needle fully exposed.
Figure 10:
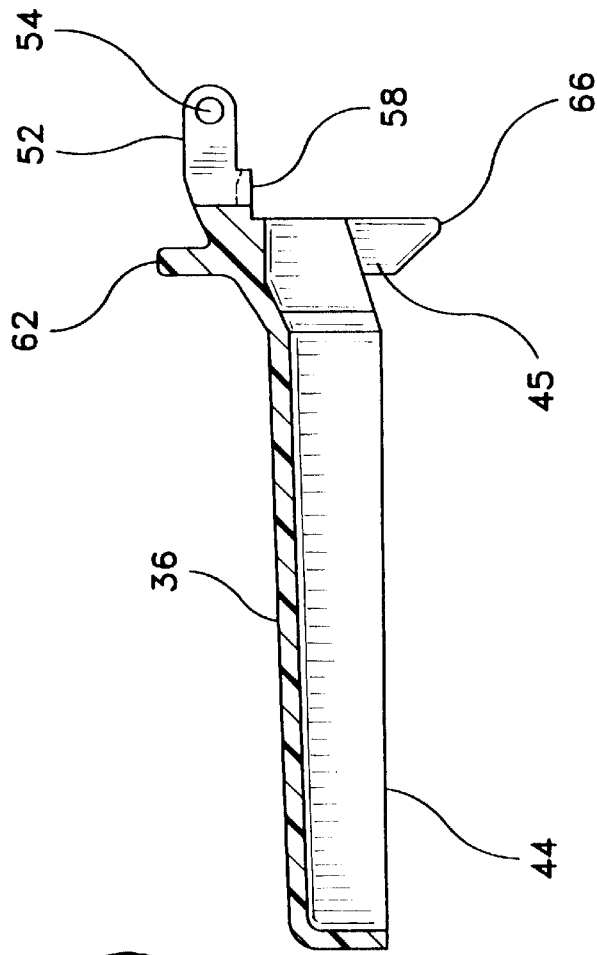
FIG. 10 is a cross-sectional view of the shield portion from the view of FIG. 5, along the line 10—10.
Figure 11:
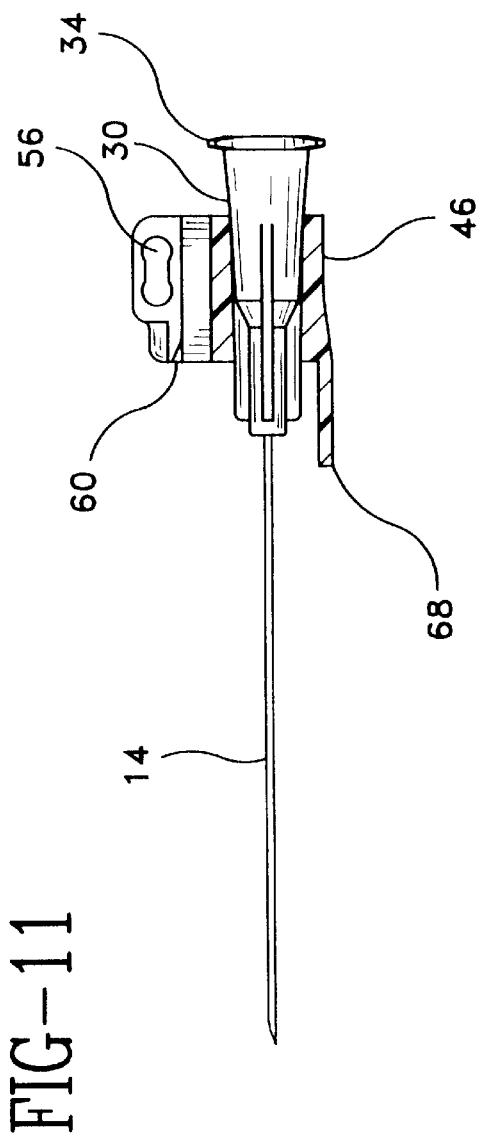
FIG. 11 is a cross-sectional view of the needle, hub, and mount from the view of FIG. 5, along the line 11—11.
Figure 12:
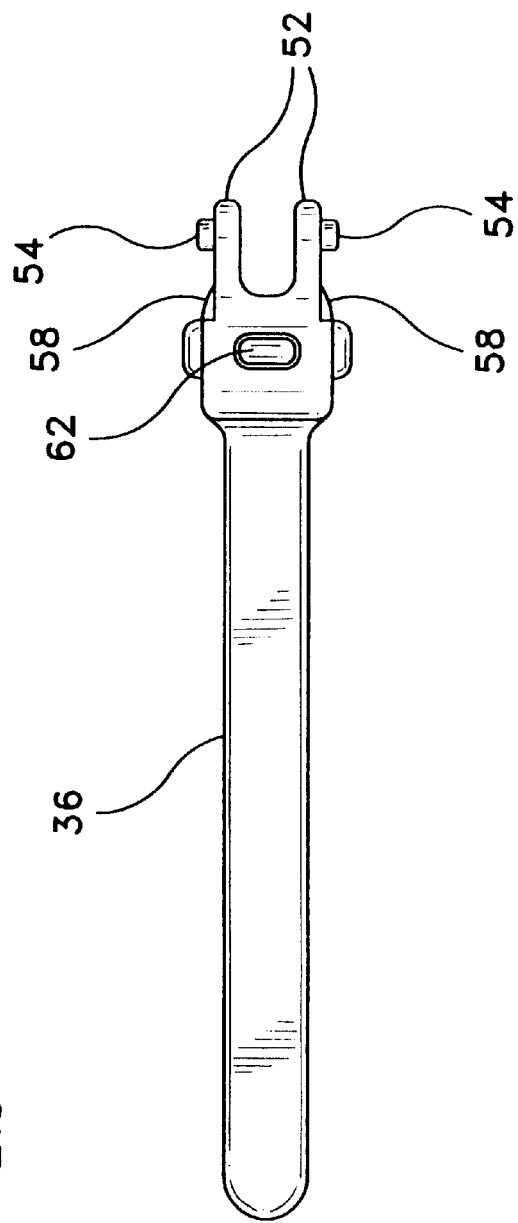
FIG. 12 is a top plan view of the shield shown in FIG. 5.
Figure 13:
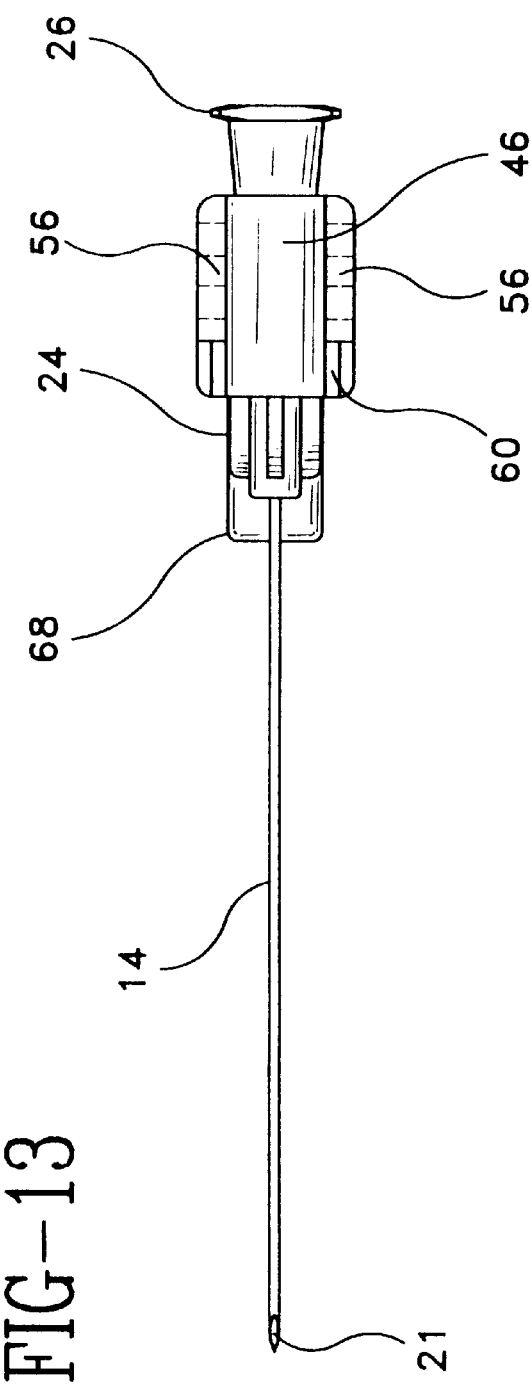
FIG. 13 is a top plan view of the needle, hub, and mount shown in FIG. 5.
Figure 15:
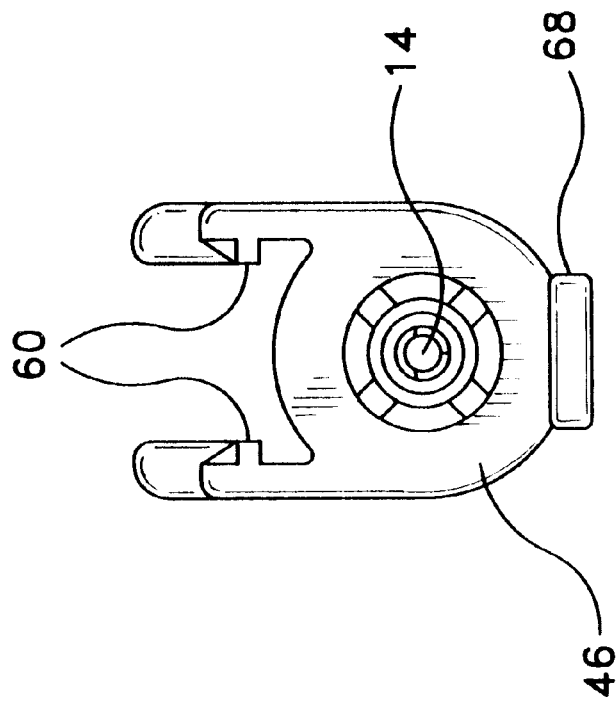
FIG. 15 is a distal end view of the needle, hub, and mount shown in FIG. 5.
Figure 14:
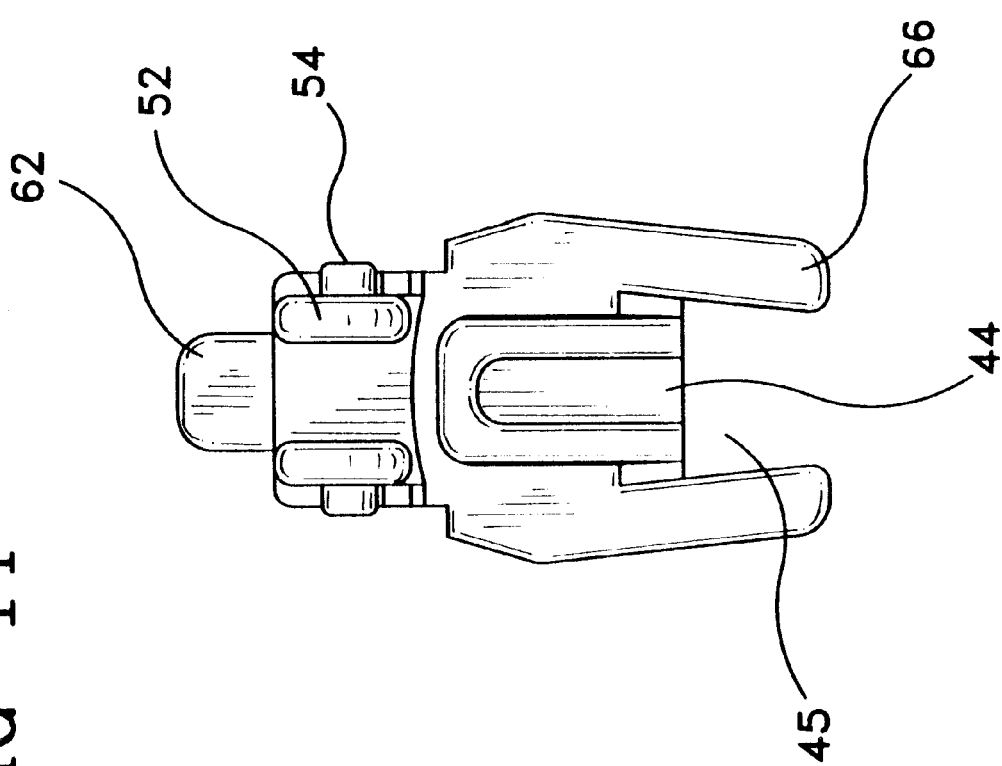
FIG. 14 is a proximal end view of the shield shown in FIG. 5.

Shielded assembly 10 of the invention preferably includes at least one first outward protuberance 62 proximally on shield 36, on sidewall 42 opposite elongate opening 44 to receive a practitioner's finger and facilitate movement of shield 36 between the closed position and latched position, as illustrated in FIGS. 6 and 7. First protuberance 62 may also serve to limit the opening of shield 36, as illustrated in FIGS. 4 and 9. Assembly 10 also includes at least one, preferably two, second outward protuberances 66 located proximally on shield 36, projecting outwardly from the same side of the shield as opening 44. Second outward protuberances 66 are also positioned to receive the practitioner's finger and facilitate movement of the shield between the closed position and the open positions, as illustrated in FIGS. 8 and 9. Second protuberances 66 also serve as a rest, when the assembly is rested on a surface, serving to keep the needle and shield elevated from the rest surface.

As is shown in FIG. 6, in preparing to use a syringe fitted with assembly 10 of the invention, the practitioner applies distal finger pressure to first protuberance 62, moving shield 36 from the latched position to the closed position shown in FIG. 7. Application of finger pressure to second protuberance 66 as shown in FIG. 8, then allows the practitioner to move shield 36 toward the opened position, as shown in FIG. 9, without having to place his hand near the distal point of the needle. When the practitioner has completed the procedure with the needle, the shield may be closed and latched without placing the practitioner's hand in close proximity to the distal needle point, substantially reducing the possibility of needle contact. To close the shield, the practitioner first applies finger pressure to protuberance 62 closing the shield, and then engages the latch by proximal movement of the shield with respect to the mount. The ability to unlatch, open, use and then close and relatch the assembly is particularly useful for hospital pharmacy usage. A syringe fitted with the assembly of the invention may be prepared with a dosage for a patient procedure, then shield 36 may be closed and latched, substantially preventing contact with the needle either by the person filling the syringe, delivering the syringe or conducting the procedure to the patient. At the procedure site, the shield is then easily unlatched, opened and the procedure completed. Then, the shield may be easily reclosed and latched in one hand, again without the need for the practitioner's hand to be in close proximity to the distal point, for disposal according to the institution's protocol.

FIGS. 10–15 allow examination of the shield, mount, hinge and latch in plan, partial cross-section and end views. FIGS. 10–15 show that mount 46 includes a brace 68 projecting distally to stiffen the attachment of shield 36 to mount 46 by fitting within a proximal portion 45 of elongate opening 44 when the shield is in the closed or latched positions. Brace 68 is located on the opposite side of the mount from slots 56 to substantially reduce off-axis movement that would tend to remove pins 54 from slots 56.

For applications where needle point bevel position is not significant, mount 46 may be fixedly mounted onto needle hub 24 by adhesive bonding, mechanical press fit, mechanical snap-fit, solvent bonding or the like. An alternative embodiment to that illustrated in FIGS. 1–15 is illustrated in FIG. 16. In this embodiment, the needle hub and the mount are integrally formed as a single unit 80 with needle 14 fixedly attached. Needle 14 may be fixedly attached into unit 80 by adhesive bonding, insert molding and other similar methods used to bond needles into standard needle hubs. Forming the mount and needle hub as single unit 80 provides a manufacturing advantage by reducing the number of parts in the assembly and is well suited for applications that do not require needle bevel orientation. In applications where needle bevel orientation is important, the needle bevel 21 may be radially oriented as it is fixedly attached into unit 80. However, radial orientation of the needle into unit 80 places an additional constraint on the manufacturing process that should be evaluated for the particular application against the efficiency gained by the reduction in the number of parts.

Figure 17:
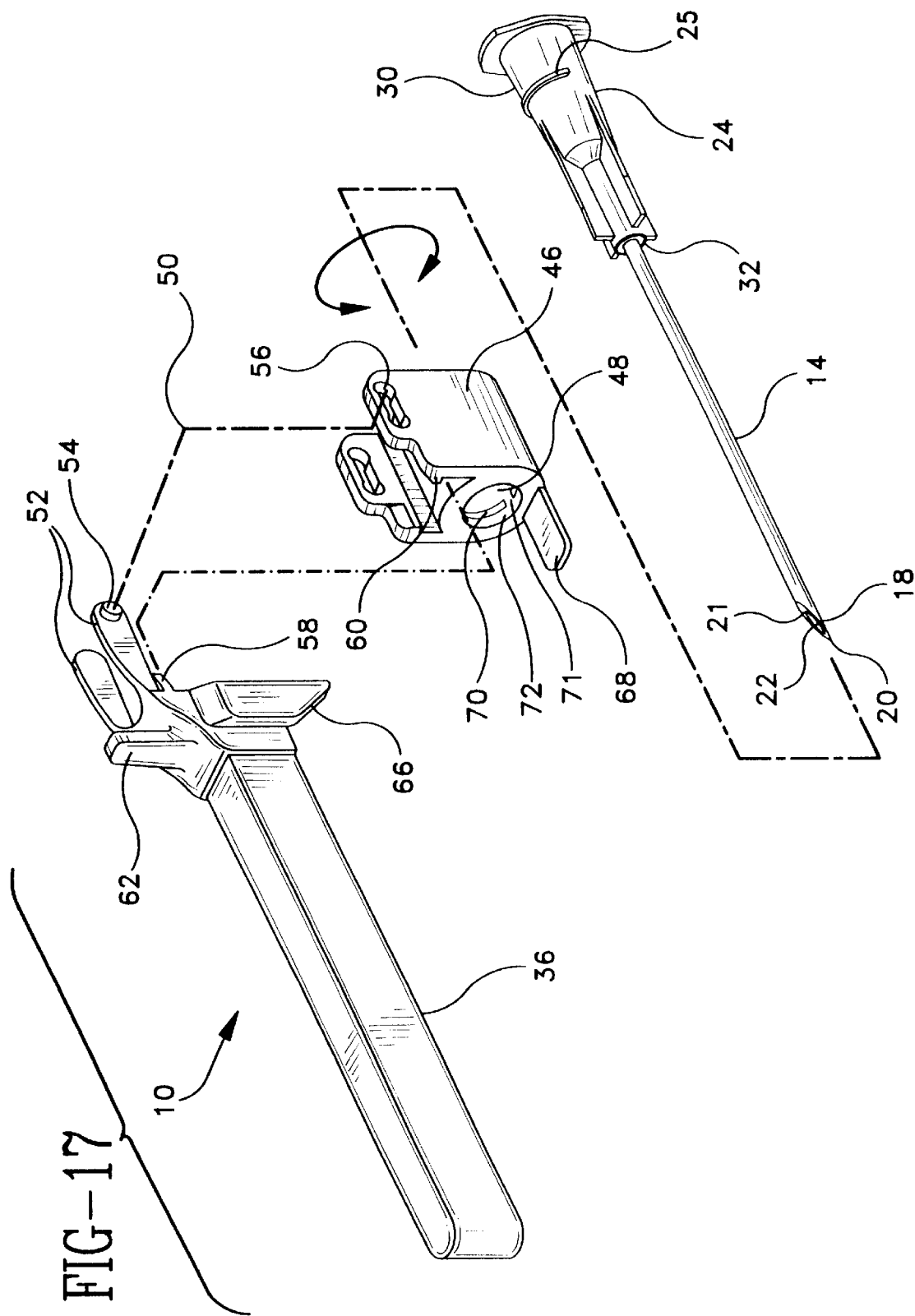
FIG. 17 is a partially exploded perspective of a more preferred embodiment of the needle assembly of the present invention.

To eliminate the need for orientation of the needle to the hub during manufacturing, a more preferred embodiment of the assembly of the invention is shown in FIGS. 17 and 18. In this more preferred embodiment, mount 46 and passage 48 include a cooperative groove and projection, as illustrated in FIGS. 17 and 18, mount 46 includes a groove 70 on an inside surface 72 of passage 48 to retain mount 46 on needle hub 24. As an example, needle hub 24 includes a projection 25 disposed to engage groove 70 when the mount is positioned on the needle hub. A needle hub with a groove disposed to cooperate with a projection on the hub is not shown to reduce the number of Figures, but is considered within the scope of the invention. When mount 46 is retained on needle hub 24 using the cooperative groove and projection, the engagement of the projection with the groove retains the mount on the hub and allows annular rotation of the shield about the hub.

The preferred ability to rotate the shield about the hub allows the practitioner to rotate the needle to a desired bevel orientation for the procedure and then rotate the open shield out of the way. The ability to orient the needle bevel is particularly important to phlebotomy procedures, because most phlebotomy protocols call for placing the needle into the patient's blood vessel at a shallow angle with the needle bevel 21 face up. Groove 70 preferably also includes a stop 71 to allow the mount to rotate less than one complete rotation about the hub to facilitate rotatable threading and unthreading for mounting and dismounting of assembly 10 on a fluid handling device.

Figure 20A:
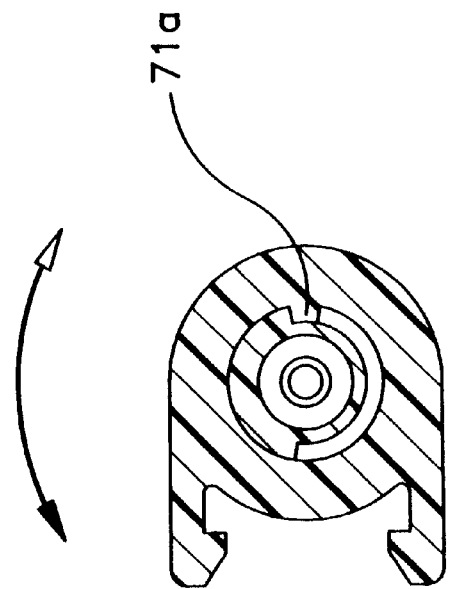
FIG. 20a is another view of the hub portion from FIG. 20 rotated 90° about the stationary needle.
Figure 20:
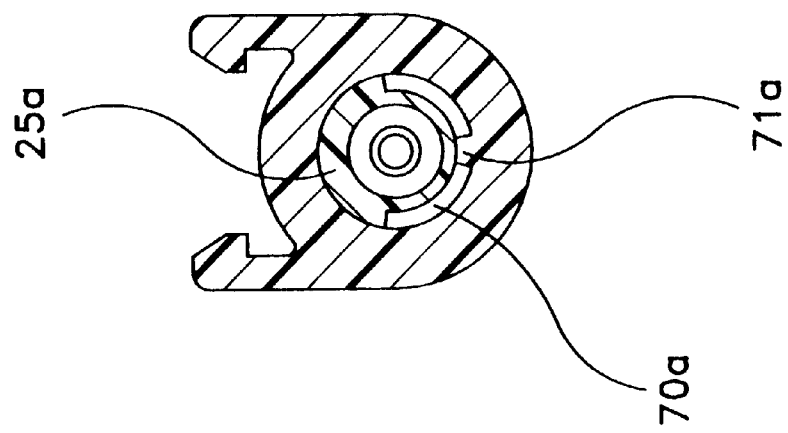
FIG. 20 is a cross-sectional view of the hub portion of the invention taken from FIG. 19 along the line 20—20.

An alternate embodiment particularly directed toward phlebotomy is shown in FIGS. 19, 20 and 20a. In this embodiment, there are elements similar in structure and function to the embodiment of the present invention shown in FIGS. 1–17. Accordingly, substantially similar components that perform substantially similar functions are numbered identically to those components of the embodiment of FIGS. 1–17 except that a suffix "a" is added to identify those components in FIGS. 19, 20 and 20a. Assembly 10a includes shield 36a and mount 46a. In this embodiment, needle 14a has a distal portion 15 with a distal point 17 and a flow control valve 19 to occlude flow through the needle. Needle hub 24a includes external distal threads 26a for mounting hub 24a into a needle holder 90. Needle holder 90 is useful for filling evacuated blood collection tubes that are mounted on the distal portion 15 of the needle and displace flow control valve 19. Referring to FIGS. 20 and 20a, cross-sectional views of hub 24a and mount 46a are illustrated. In FIG. 20, mount 46a is shown at one position with respect to needle hub 24a, and in FIG. 20a, mount 46a is shown rotated about 90° with respect to needle hub 24a. In FIGS. 20 and 20a, stop 71a to limit the rotation of mount 46a with respect to hub 24a is also shown.

The shield, mount, and needle hub of the invention may be formed from polymeric materials such as thermoplastic resins, cast resins and the like. Suitable thermoplastic resins include, but are not limited to, polypropylene, polyethylene, acrylonitrile-butadiene-styrene, polycarbonate, polystyrene and the like. Polypropylene and polyethylene are preferred thermoplastic resins. For some applications, polycarbonate resin may be preferred for applications where transparency and rigidity are required. Needles suitable for use in the assembly may be formed from stainless steel. In assembly 10, needle 14 is fixedly attached to hub 24. Suitable methods for fixedly attaching the needle to the hub include, but are not limited to, adhesive bonding and insert molding the needle into the hub. Preferably, needle 14 is adhesively bonded into hub 24.

The shielded needle assembly of the invention is simple to manufacture and easy to use. The assembly allows practitioners to reshield needles and latch the shield substantially without placing their hands in close proximity to, or beyond, the distal point of the needle, thus encouraging the practitioners to cover the needle after use. In clinical settings where pointed needles are routinely used, use of shielded assemblies of the invention may provide reductions of exposures to unshielded needles to both practitioners using needles and to support personnel who may encounter used needles.

What is claimed is:

1. A needle assembly comprising:

an elongate needle having a proximal end, a distal end and a passageway therethrough;

a needle hub having a proximal end, a distal end and an outside surface, said needle hub having an axial opening therethrough to receive and hold said proximal end of said needle at said distal end of said needle hub with said distal end of said needle projecting distally axially therefrom, said proximal end of said needle hub further including means for releasably mounting said needle hub on a fluid handling device;

a shield having a proximal open end, a distal end, a sidewall having an elongate opening from said distal end to said proximal end, said shield being operative between an open position, wherein said needle is exposed for use by passage through said elongate opening, a closed position, wherein said shield substantially obstructs access to said needle, and a latched position wherein said shield is substantially prevented from inadvertent movement to said open position;

hinge means for retaining said shield onto said needle hub, said hinge means including a mount, said shield movable between said open position and said closed position over said needle by an off-axis pivotal movement about said hinge means, and when said shield in said closed position said shield being movable between said closed position and said latched position by an axial movement of said shield with respect to said mount;

said hinge means further comprising two arms projecting proximally axially from said proximal end of said shield, each arm having a perpendicularly extending peg, and said mount having a pair of elongate slots sized and disposed to receive said pegs thereby forming a pivot and attaching said shield to said mount, said shield being latched and unlatched with axial movement of said shield with respect to said mount; and said mount further including operative latch means for releasably latching said shield when said shield is moved proximally from said closed position to said latched position.

2. The needle assembly of claim 1 wherein said operative latch means comprises at least one tab that projects outwardly on said proximal end of said shield and at least one ledge on said mount, said tab and said ledge disposed to releasably engage when said shield is in said latched position to help prevent pivotal movement of said shield to the open position, said tab and said ledge disposed to be disengaged when said shield is in said closed position, thereby allowing pivotal movement of said shield between said closed position and said open position.

3. A needle assembly comprising:

an elongate needle having a proximal end, a distal end and a passageway therethrough;

a needle hub having a proximal end, a distal end and an outside surface, said needle hub having an axial opening therethrough to receive and hold said proximal end of said needle at said distal end of said needle hub with said distal end of said needle projecting distally axially therefrom, said proximal end of said needle hub further including means for releasably mounting said needle hub on a fluid handling device;

a shield having a proximal open end, a distal end, a sidewall having an elongate opening from said distal end to said proximal end, said shield being operative between an open position, wherein said needle is exposed for use by passage through said elongate opening, a closed position, wherein said shield substantially obstructs access to said needle, and a latched position, wherein said shield is substantially prevented from inadvertent movement to said open position;

hinge means for retaining said shield onto said needle hub, said hinge means including a mount, said shield movable between said open position and said closed position over said needle by an off-axis pivotal movement about said hinge means, and when said shield in said closed position said shield being movable between said closed position and said latched position by an axial movement of said shield with respect to said mount;

said hinge means for retaining said shield onto said needle hub further comprises an annular groove on an exterior surface of said needle hub and a projection on an inside surface of said axial opening in said mount disposed and sized to engage said groove when said portion of said needle hub is positioned in said opening, said engagement of said projection and said groove retaining said mount on said hub and allowing annular rotation of said mount about said hub; and said groove and said projection further including limit means to limit said annular rotation of said mount about said hub to less than about one rotation, thereby facilitating a threading and an unthreading of said hub for mounting and dismounting of said assembly to fluid handling devices.

4. The needle assembly of claim 3 wherein said limit means for limiting said rotation of said mount about said hub includes a stop in said groove positioned to engage said projection and limit said rotation of said mount about said hub to less than one complete rotation.

* * * * *